United States Patent [19]

Kenny

[11] Patent Number: 5,171,322

[45] Date of Patent: Dec. 15, 1992

[54] STABILIZED MENISCUS PROSTHESIS

[76] Inventor: Charles H. Kenny, 510 North St., Pittsfield, Mass. 01201

[21] Appl. No.: 794,224

[22] Filed: Nov. 19, 1991

Related U.S. Application Data

[62] Division of Ser. No. 479,565, Feb. 13, 1990, Pat. No. 5,092,894.

[51] Int. Cl.$^5$ .............................................. A61F 2/30
[52] U.S. Cl. ....................................... 623/18; 623/20
[58] Field of Search .................................... 623/18, 20

[56] References Cited

U.S. PATENT DOCUMENTS

| | | | |
|---|---|---|---|
| 3,927,423 | 12/1975 | Swanson | 3/1.91 |
| 4,344,193 | 8/1982 | Kenny | 623/20 |
| 4,880,429 | 11/1989 | Stone | 623/18 |
| 4,919,667 | 4/1990 | Richmond | 623/18 |

Primary Examiner—David Isabella
Assistant Examiner—Debra S. Brittingham
Attorney, Agent, or Firm—Nixon & Vanderhye

[57] ABSTRACT

A meniscus prosthetic device replaces natural components of a condylar joint and includes a body and a tail. The body is of biocompatible, deformable, flexible and resilient material for bearing compressive loads and for translating the loads to tensile stress. The tail is also biocompatible material and extends as a continuation of the body from a first end to a second end of the body. The tail provides a continuous loop circuit for the propagation of tensile (hoop) stresses from the body, and provides stabilization of the knee joint and proprioceptive feedback. The prosthesis is implanted in a human knee in a position to take the place of a naturally occurring meniscus between one femoral condyle and the corresponding tibia, and the tail is placed into contact with bone associated with the knee. The body will be stabilized against unphysiological motions or deviations, yet movement of the body to achieve constant conformation to the femoral condyle and tibia under torsional, translational, and compressive loading is provided.

20 Claims, 4 Drawing Sheets

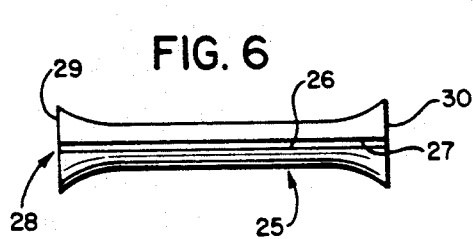
FIG. 6
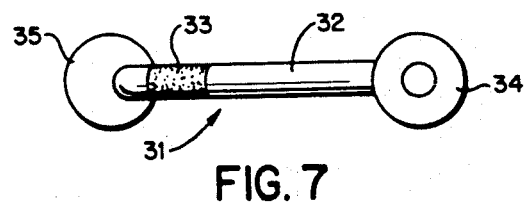
FIG. 7
FIG. 8
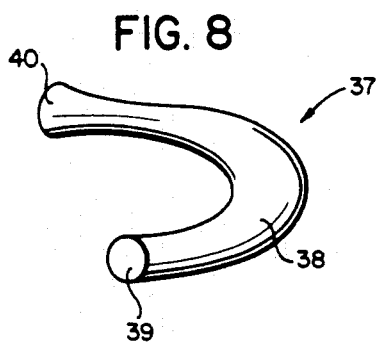
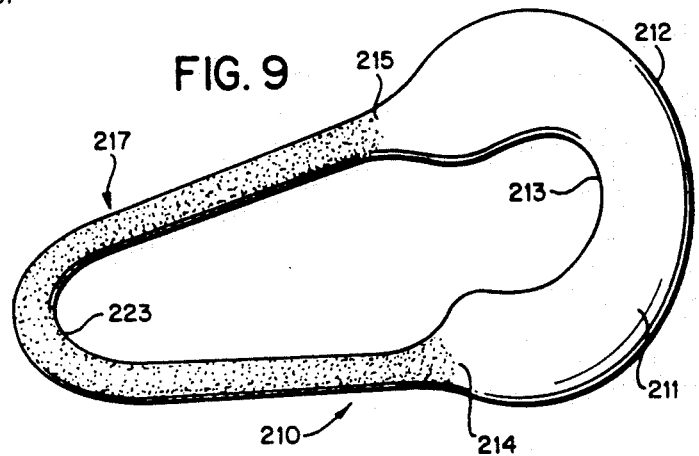
FIG. 9
FIG. 10
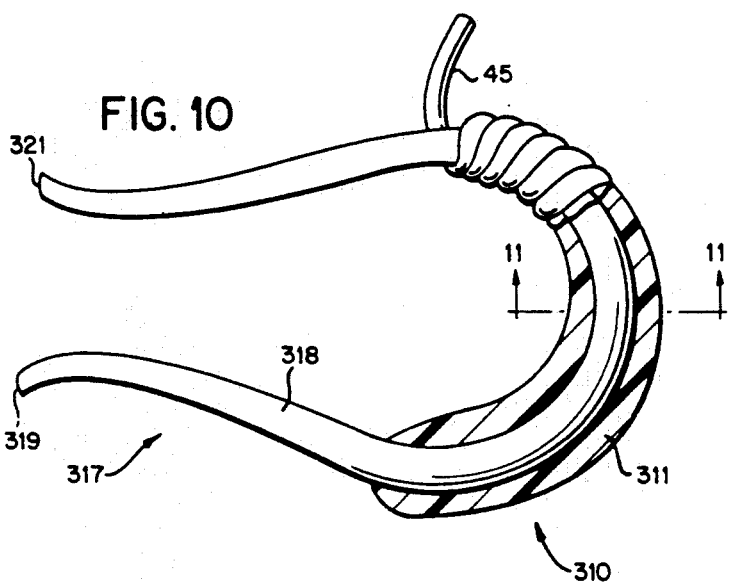
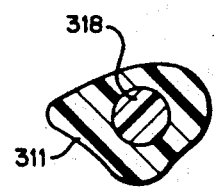
FIG. 11

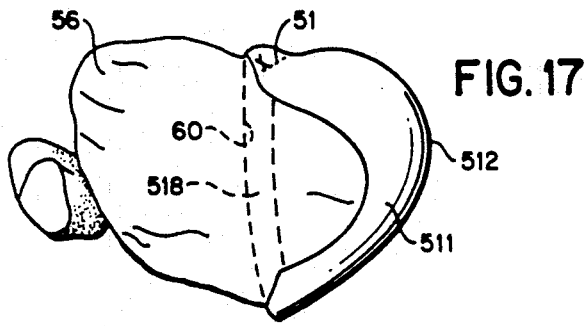
FIG. 17
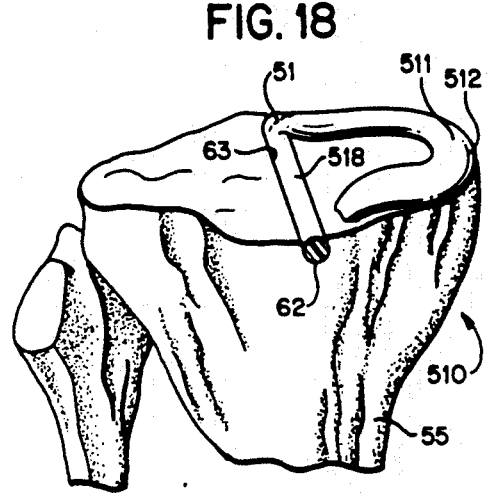
FIG. 18
FIG. 19
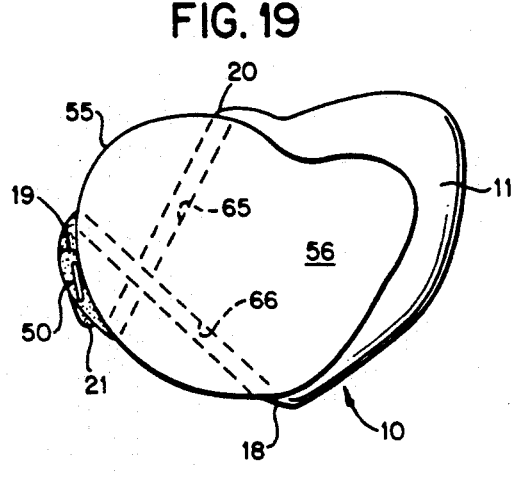
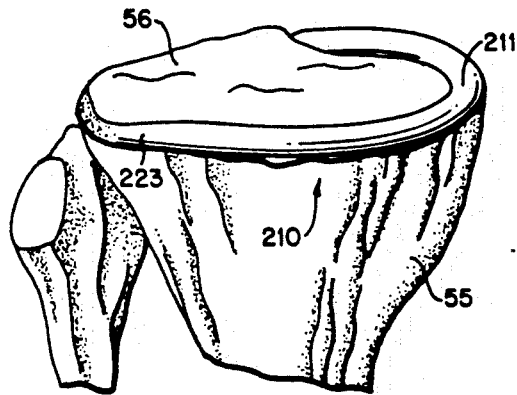
FIG. 20
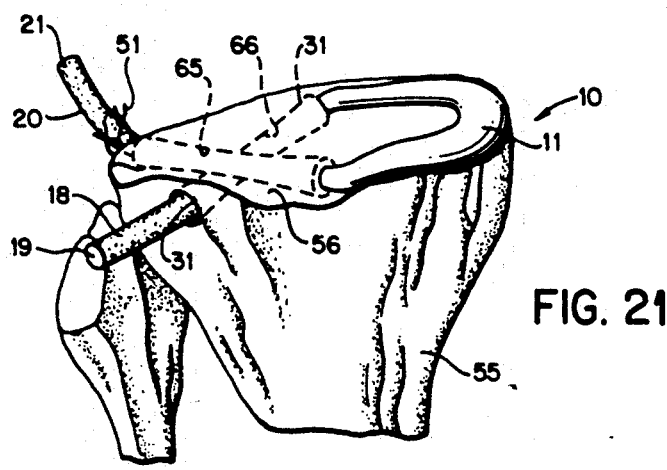
FIG. 21

STABILIZED MENISCUS PROSTHESIS

This is a division of application Set. No. 07/479,565, filed Feb. 13, 1990, now U.S. Pat. No. 5,092,894.

Recent advances in medical science and biological engineering have made a meniscus prosthesis more practical. A desirable form of meniscus prosthesis is shown in U.S. Pat. No. 4,344,193 (the disclosure of which is hereby incorporated by reference herein). While the device illustrated in that patent has many practical advantages, it has not yet been extensively utilized in actual human knees.

According to the present invention a device—and a method of implantation thereof—are provided that have the same advantages of the meniscus prosthesis disclosed in the U.S. Pat. No. 4,344,193 patent, and additionally have other advantages. In addition to the advantages contained in the patent, the prosthesis according to the invention stabilizes the knee joint against unphysiological motions or deviations. It especially provides for stabilization in conjunction with ligamentous reconstructions. Further, and perhaps most significantly, the prosthetic device according to the invention translates compression and torsional loads into tensile or "hoop" stresses in the prosthesis.

The prosthetic device according to the invention has two major components, a body, and a tail means. The body is very similar to the body in the U.S. Pat. No. 4,344,193 patent only without the raised prominences. The body is of biocompatible, deformable, flexible and resilient material such as silicone rubber, or a number of natural materials (e.g. collagen, tendon or fibrocartilage). It has an arcuate construction, of significantly less than 360° but at least about 150°. The cross-sectional area of the radial exterior is greater than the cross-sectional area of the radial interior; that is the body has a shape, when implanted, of a naturally occurring meniscus. The body bears the compressive loads of the femoral condyle against the tibia, translates those loads to the tail means as tensile stresses, stabilizes the femoral condyle on the tibia, lubricates and aids in the metabolism of the articular surfaces of the joint, and expands and presses against the soft tissues around the joint. It also may serve as an attachment of the prosthesis to the soft tissues surrounding the joint.

The tail means may have a variety of constructions. Preferably the tail means provide a continuous loop, either being formed as an integral loop originally with the body, or being connected to the ends of the body and ultimately being attachable together at free ends thereof, or being connected at one end of the body and being attachable at the free end thereof to the other end of the body. The tail means provides a continuous loop circuit for the the propagation of tensile (hoop) stresses, provides soft tissue anchorage for stability (particularly against unphysiological motions or deviations), and provides proprioceptive feedback. Proprioceptive feedback or "joint position sense", is an important physiological mechanism which assists in preventing injury. The tail means also may allow for expansion and gliding to conform to the torsional, translational, and compressive loading of the prosthesis. In use the tail means is not truly attached to the bone, although it is placed in operative association therewith. Motion between the tail means and the bone must be allowed so that the prosthesis may elongate and shorten as tension is developed within it by compressive loading of the knee.

The tail means typically will be disposed in an aperture in surrounding bone, such as a bony trough, through-extending bore, channel, or the like. In some circumstances it is desirable to have a sleeve surrounding a portion of the tail means that is disposed in operative association with the bone. The sleeve allows for gliding movement of the prosthesis with respect to the bone while still providing for "locking" or "anchoring" of the prosthesis with respect to the bone. A polyethylene tube may serve as a gliding sleeve, or the outer surface thereof may be coated with Dacron mesh or metal porous material to allow soft tissue or bony ingrowth, respectively. The sleeve also may serve as a point for suture fixation.

The tail may be completely integral with the body, or may be formed of a separate material. In fact the body may be formed around a portion of the tail (which could be in the form of a hoop or strip). The tail has substantial thickness, on the order of at least 30% of the cross-sectional area of the body. This clearly distinguishes it from prior art prostheses which may have sutures extending therefrom, which sutures are thin and are not capable of performing the functions of the tail of the prosthesis according to the invention. It is desirable that the tail have a smaller cross-sectional area than the body, but it may have a cross-sectional area 100% that of the body.

The invention also comprises a method of implanting a meniscus prosthetic device in a human knee, the prosthetic device having an arcuate body of biocompatible, deformable, flexible, and resilient material, and a tail for stabilizing the body. The method comprises the steps of: (a) Inserting the body into position in the knee to take the place of a naturally occurring meniscus between one femoral condyle and the corresponding tibia. (b) Placing the tail into contact with bone associated with the knee so that the tail will stabilize the body in the knee against unphysiologic motions or deviations, yet allowing movement of the body to achieve constant conformation to the femoral condyle and tibia under torsional, translational, and compressive loading. And (c), attaching the device to soft tissue surrounding the knee joint.

The device—as described above—used in the method according to the invention preferably comprises a tail integral with the body and comprising a continuous uninterrupted extension of the body, defining a closed loop, and a trough is either formed or naturally existing in the bone surrounding the knee joint. In such situations, step (a) is practiced by distracting the femoral condyle and tibial surfaces, and passing the device between them, and step (b) is practiced by placing the tail in the bony trough. The trough may be in a central portion of the bone, or around the periphery of the bone.

Where the body has first and second ends with the first tail member extending integrally from the first end and a second tail member extending integrally from the second end, with the tail members having free ends, then step (b) is practiced by passing the tail members into operative association with openings in bone (e.g. drilled through-extending openings) surrounding the knee joint, and then affixing the free ends of the tail members together. Alternatively, the tail members could be passed through sleeves, and knotted at the free ends thereof to prevent passage through the openings.

It is the primary object of the present invention to provide a useful and effective meniscus prosthesis, and method of implantation thereof. This and other objects of the invention will become clear from an inspection of the detailed description of the invention, and from the appended claims.

BRIEF DESCRIPTION OF THE DRAWINGS

FIG. 6 is a side view of one form of gliding sleeve according to the invention;

FIG. 7 is a side view of a second form of gliding sleeve;

FIG. 8 is a side view of a third form of gliding sleeve—a flexible gliding sleeve—according to the invention;

FIG. 9 is a top plan view of a third embodiment of prosthetic device according to the invention;

FIG. 10 is a top view, partly in cross-section and partly in elevation, of a fourth form of prosthetic device according to the invention shown during construction of the last portion thereof;

FIG. 11 is a cross-sectional view taken along lines 11—11 of FIG. 10;

FIG. 17 is a top view of FIG. 16 with the femur not shown for clarity of illustration;

FIG. 18 is a view like that of FIG. 16 only showing the prosthesis tail positioned in a different manner, and with a part of the prosthesis cut away for clarity of illustration;

FIG. 19 is a top plan view of the prosthesis of FIG. 1 shown in association with the tibia;

FIG. 20 is a top perspective schematic view of the prosthesis of FIG. 9 shown in association with a human tibia; and FIG. 21 is a view like that of FIG. 20 only showing the prosthesis of FIG. 1 in association with a tibia and a gliding sleeve, during implantation.

DETAILED DESCRIPTION OF THE DRAWINGS

Figure 2:
FIG. 2 is a cross-sectional view taken along lines 2—2 of FIG. 1.

An exemplary meniscus prosthesis according to the invention is shown generally by reference numeral 10. The meniscus prosthetic device 10 is for preventing and reversing degenerative changes in a human knee, comprising means for replacing natural components of a condylar joint so that the articular cartilage remains intact. The device 10 comprises an arcuate body 11 of biocompatible, deformable, flexible and resilient material. It has a radial exterior portion 12 and a radial interior portion 13, and first and second ends 14, 15, respectively. As is the meniscus prosthesis in U.S. Pat. No. 4,344,193, the prosthesis 10 may be made of silicone rubber or a comparable material. Alternatively, it may be made of natural substance such as a piece of animal tissue (such as collagen, tendon, or fibrocartilage), or a part of human tissue harvested from the patient's own body, such as periosteal tissue turned inside out, or part of a tendon. The body 11 has a shape, when implanted, of a naturally occurring meniscus; that is, preferably the cross-sectional area of the radial exterior 12 is greater than that of the radial interior 13, with a generally constant slope therebetween, as most clearly illustrated in FIG. 2.

Figure 1:
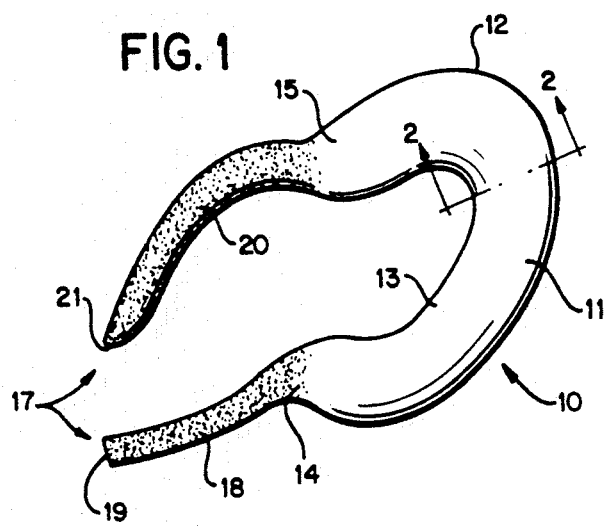
FIG. 1 is a top perspective schematic view of a first embodiment of a prosthetic device according to the invention.

The second part of the prosthetic device 10 comprises the tail means, shown generally reference numeral 17 in FIG. 1. In this particular embodiment the tail means comprises two tail portions 18, 20. The first tail portion 18 has a free end 19 and is attached to the first end 14 of the body 11. The second tail portion 20 has a free end 21 and is attached and integral with the second end 15 of the body 11. The tail means 17 may be of the same material as the body 11, or a different material. The material of the tail means 17 need not be as flexible or deformable as the material of the body 11 (e.g. a fabric type material).

In use, the tail means 17 will be used to stabilize the body 11, by placing it in operative association (although not rigidly attaching it to) surrounding bone in a human knee joint. In the most typical situation, the free ends 19, 21 of the tail will be attached together as with a clip, stitching, or staple.

It is desirable that the tail means 17 have a smaller cross-sectional area than the body 11, although that is not absolutely necessary and under some circumstances the tail having the same approximate cross-sectional area may be utilized. Preferably the tail 17 has a cross-sectional area at least 30% of that of the body 11, distinguishing it from mere sutures extending outwardly from a prosthesis.

The prosthesis 10 according to the invention achieves the same advantages as the prosthesis in U.S. Pat. No. 4,344,193. Additionally it stabilizes the knee joint against unphysiologic motions or deviations, particularly in conjunction with ligamentous reconstructions. Also, the compression and torsional loads born by the meniscus will be sustained by the circular or hoop shape of the prosthesis 10, which will thereby translate such loading patterns into tensile ("hoop") stresses in the prosthesis.

The primary functions of the tail means 17 are to provide a continuous loop circuit for the propagation of tensile (hoop) stresses, to provide soft tissue anchorage for stability and proprioceptive ("joint position sense") feedback, and to allow for expansion and gliding to conform to the torsional, translational, and compressive loading of the prosthesis. Thus the prosthesis will be able to follow the femoral condyle in motions across the tibia.

The main functions of the body 11 are to bear the compressive loads of the femoral condyle against the tibia, to translate these loads to the tail means as tensile stress, and to stabilize the femoral condyle on the tibia. Also the body 11 serves to lubricate and aid in the metabolism of the articular surfaces of the knee joint, to expand and press against the soft tissue surrounding the joint, and to serve as an attachment of the prosthesis to the soft tissues around the joints.

Figure 3:
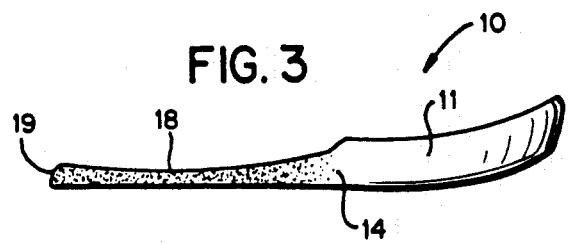
FIG. 3 is a side view of the prosthesis of FIG. 1.
Figure 4:
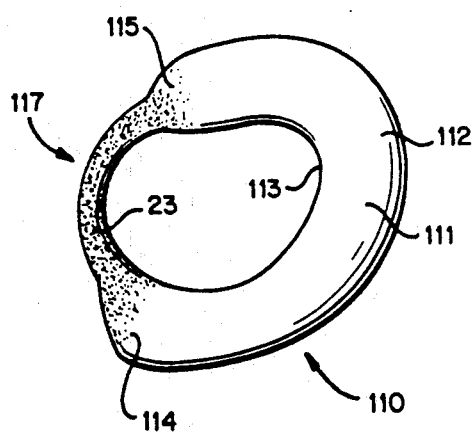
FIG. 4 is a top plan view of a second embodiment of prosthesis according to the invention.
Figure 5:
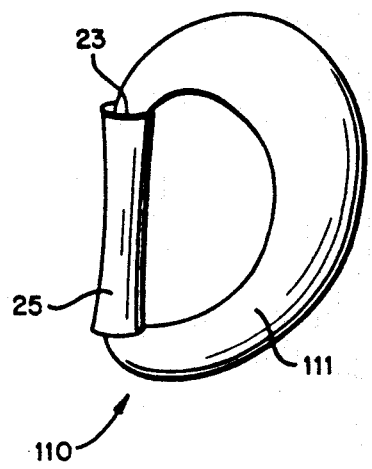
FIG. 5 is a view comparable to that of FIG. 4 only with the addition of a gliding sleeve around the tail portion of the prosthesis of FIG. 4.

FIGS. 4 and 5 illustrate another form of prosthetic device according to the invention. In FIGS. 4 and 5 the same structures as in the FIGS. 1 through 3 embodiment are shown by the same reference numeral only preceded by a "1". Note that the major distinction of the prosthetic device 110 over that of the FIGS. 1 through 3 embodiment is that the tail means 117 comprises a continuous closed loop (i.e. there are no free ends). That is a continuous tail 23 is provided integral with the body 111 at both the ends 114 and 115 thereof. In the FIG. 5 embodiment, the structure is identical except that a gliding sleeve member 25 has been placed over the tail 23. The sleeve 25 is also shown in FIG. 6, and comprises a tubular member of a biocompatible material, one particular material that is useful being polyethylene. The sleeve 25 must be constructed so that it can be placed over the tail 23 since the tail 23 forms a continuous loop with the body 111. This is accomplished by providing a longitudinal slit 28 (see FIG. 6) in the tube, defined by edge portions 26, 27 of the tube 25. The tube 25 is obviously open at the ends 8, 30 thereof. By pulling part the surfaces 26, 27 they may be placed over the tail 23, and closed in place so that the sleeve 25 surrounds the tail 23 (see FIG. 5).

Other forms that sleeves according to the invention could take are illustrated in FIGS. 7 and 8. The sleeve 31 in FIG. 7—rather than being straight, as is the sleeve 25—is oblique. It includes a main tubular body 32 with open ends 34, 35. A coating 33 may be applied to the body 32. The coating may be applied along the entire length, or just a portion of the length, of the body 32 and may be a Dacron mesh to allow for soft tissue ingrowth, or a metal porous coating to allow for bony in-growth.

Another form of sleeve is illustrated by reference numeral 37 in FIG. 8 comprising a body 38 and open ends 39, 40. As illustrated in FIG. 8, the body 38 is of flexible material so that it can be bent into any configuration desired (although in a relaxed condition it is preferably straight, although an arcuate memory may be imparted thereto for specific situations). The function of the sleeves 25, 31, 37 is to allow gliding movement of the tail means 17, 117 with which they are associated while still allowing "attachment" to a bone. The sleeves are designed to be placed within bony openings, such as troughs, channels, or through-extending passageways. The prosthesis 10, 110 is never rigidly attached to a bone, but rather—whether or not a sleeve is utilized—is positioned so that it can move in response to loadings, e.g. it must be able to elongate and shorten.

Additional embodiments of prosthetic devices according to the invention are illustrated in FIGS. 9 through 15. In each embodiment portions thereof comparable to the FIGS. 1 or 4 embodiments are shown by the same two digit reference numeral only preceded by another reference numeral (e.g. "2" for the FIG. 9 embodiment).

The FIG. 9 prosthetic device 210 is similar to the device 110 except that the tail means 217 comprises a longer tail member 223 forming a continuous loop with the body 211. FIG. 10 shows a prosthetic device 310 where the body 311 is formed around the tail body 318 (having ends 319 and 321). As illustrated in FIG. 10 at the top portion thereof, a strip of material 45 (e.g. deformable material such as silicone rubber) is being wrapped around the "tail" 318 which is at the core of the entire device 310 (see FIG. 11). The strip of material 45 may be affixed at both ends thereof to the core 318 by adhesive, sewing, melting, or any other suitable means.

The device 410 is similar to the device 10, except that the exact configuration of the end portions 414, 415 of the body 411 are slightly different, as is the cross-sectional configuration of the body 411 (although it still has a larger cross-sectional dimension at the radial exterior 412 than at the interior 413). Also the arcuate extent of the body 411 is somewhat less. In general, the arcuate extent of the body of any of the prosthetic devices according to the invention will be substantially less than 360°, although at least about 150° and preferably at least about 180°.

Figure 12:
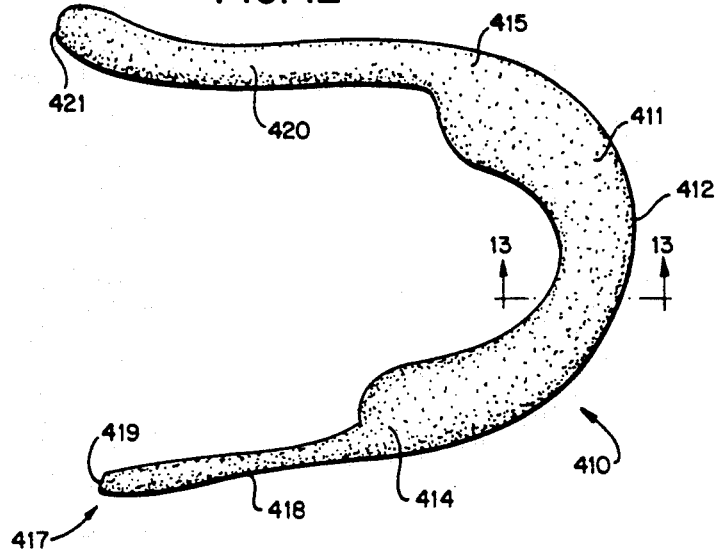
FIG. 12 is a top plan view of yet another embodiment of a prosthetic device according to the invention.
Figure 13:
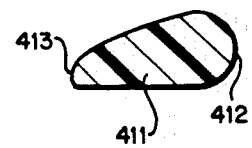
FIG. 13 is a cross-sectional view taken along lines 13—13 of FIG. 12.
Figure 14:
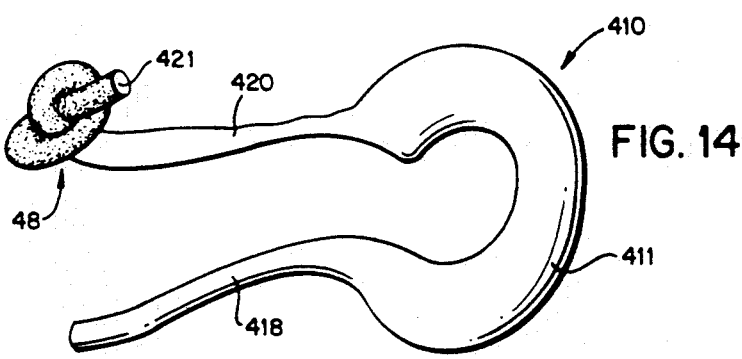
FIGS. 14 and 15 are top plan views of two still further embodiments of meniscus prostheses according to the invention.

FIG. 14 illustrates the device 410 of FIGS. 12 and 13, only showing a knot 48 being formed in the tail portion 420 thereof. When a knot is utilized to prevent withdrawal of the free end 421 of the tail 420 from a bony opening, a sleeve (e.g. sleeve 25) preferably is utilized around the tail 420. In such a circumstance even though the tails 420, 418 do not make a complete loop, tensile loading is still absorbed as changes in conformation of the knot 48 or gliding of the tail 420 within the sleeve, rather than as a hoop stress.

Figure 15:
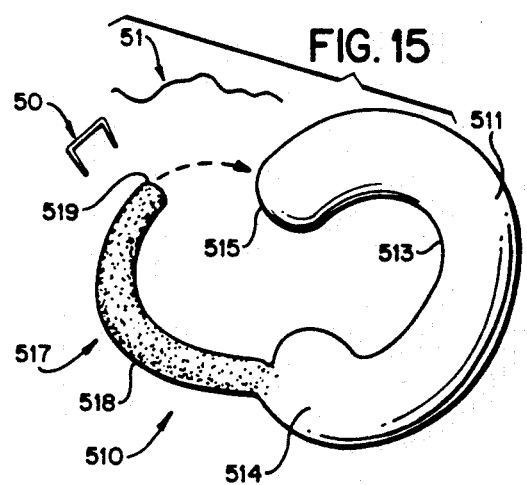

FIG. 15 illustrates another prosthetic device 510 which has a tail 518 integral with the first end 514 thereof, but with no tail at the second end 515 thereof. The free end 519 of the tail 518 will be secured to the second end 515 of the body 511 during implantation, as with a conventional clip 50 or stitching thread 51.

In all of the embodiments, the body, tail, or both may be constructed so that they allow for tissue growth into operative association therewith, and attachment to the natural tissue, in the same manner as for the prosthesis described in said U.S. Pat. No. 4,344,193.

FIGS. 16 through 21 show various manners of implantation of prosthetic devices 10-510 according to the invention. In each case, during implantation of the meniscus prosthetic device in a human knee, the tail is placed in operative association with bones surrounding the knee joint. Implantation may be accomplished by surgical or arthroscopic surgical techniques.

Figure 16:
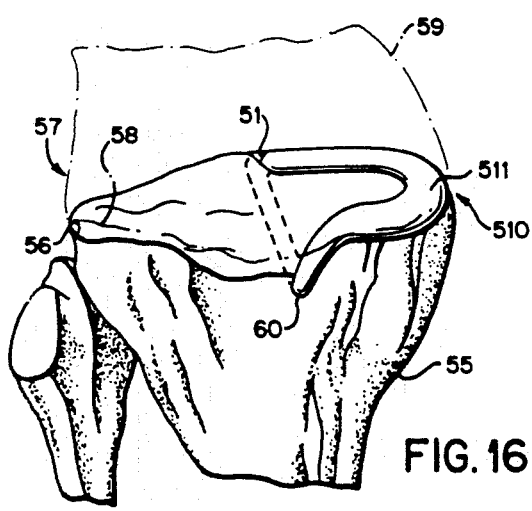
FIG. 16 is a top perspective schematic view showing the prosthesis of FIG. 15 in association with the tibia (solid line) and femur (dotted line) of a human knee.

FIGS. 16 and 17 show the prosthesis 510 in association with a tibia 55 having a surface 56 which may comprise or include articular cartilage. The knee joint 57 is provided between the tibia 55 and the inner condyle 58 of the femur 59. A through-extending passageway 60 has been formed through the tibia 55 by drilling, and the tail 518 has been inserted therethrough and then stitched by stitching 51 to the second end 515 of the body 511 of the prosthesis 510.

FIG. 18 illustrates the prosthesis 510 secured in a slightly different manner to the tibia 55. In this case, the tail 518 is disposed in a pre-existing or formed bony trough 62 having an open top 63. The trough 62 may be formed so that it has a maximum interior diameter or cross-sectional area greater than the width of the open top 63 thereof so that once the tail 518 is forced into place it will not easily come out of the body trough 62. While the prosthesis 510 is illustrated in FIG. 18 it is readily apparent that the prosthesis 110 could equally well be used, the tail 23 thereof merely being forced into the bony trough 62.

FIG. 19 illustrates the prosthesis 10 in association with the tibia 55. In this particular situation note the cross bores 65, 66 which are through-extending holes that have been drilled. The tails 18, 20 are inserted in the bores 66, 65, respectively, and then connected together at the free ends 19, 21 thereof as by the clip 50.

FIG. 20 shows the prosthesis 210 disposed in operative association with the tibia 55. Note that the embodiment illustrated in FIG. 20, the prosthesis 210 covers the entire top circumference of the bone 56, either the natural configuration of the bone thereat or a channel formed therein forming a bony trough which retains the tail 223 in place.

Note that in the utilization of any of the embodiments of the prosthesis which have a continuous loop (e.g. 110, 210), during implantation the body (e.g. 111, 211) is inserted in position in the knee to take the place of a naturally occurring meniscus between one femoral condyle and the corresponding tibia by distracting the femoral condylar and tibia surfaces, and passing the device therebetween. The tail (23, 223) is then placed in a bony trough (e.g. 62).

The FIG. 21 embodiment shows the prosthesis 10 being placed in operative association with the tibia 55 in the same manner as in FIG. 19, only showing a sleeve 31 also in use. Note that the sleeve 31 is attached by sutures 51 to surrounding tissue. The free ends 21, 19 ultimately are joined by stitching or the like, and the sleeve 31 allows free gliding movement of the tails 18, 20 with respect to the tibia 55.

While the tail is placed into contact with the bone to stabilize the body and the knee against unphysiological motions or deviations, movement of the body to achieve constant conformation to the femoral condyle and tibia under torsional, translational, and compressive loading is provided. Typically while the prosthetic device is not attached to bone, it may be attached to soft tissue surrounding the knee joint, by sutures, or by providing a porous border of any portion of the device, to allow fibrous tissue in-growth into the porous border, as described in said patent U.S. Pat. No. 4,344,193. The invention is not limited to the fixation means described above, but rather may include other types, including a plug in a hole through which the tail passes.

It will thus be seen that according to the present invention a meniscus prosthetic device, and a method of implantation thereof, have been provided which have numerous advantages. While the invention has been herein shown and described in what is presently conceived to be the most practical and preferred embodiment thereof it will be apparent to those of ordinary skill in the art that many modifications may be made thereof within the scope of the invention, which scope is to be accorded the broadest interpretation of the appended claims so as to encompass all equivalent structures and procedures.

What is claimed is:

1. A meniscus prosthetic device to prevent and reverse degenerative changes in a human knee, for replacing natural components of a femoral condylar joint so that articular cartilage therein remains intact, said device comprising:
an arcuate body of biocompatible, deformable, flexible and resilient material for bearing compressive loads and for translating the loads to tensile stress, and for stabilizing the femoral condyle, and to lubricate and aid in metabolism of articular surfaces of a knee joint, said body having first and second ends, and a radial exterior portion and a radial interior portion, and a maximum cross-sectional area portion; and
tail means of biocompatible material extending as a continuation of said body from each of said first and second ends thereof, for providing a continuous loop circuit for propagation of tensile stresses from said body, for providing stabilization of the knee joint, and for providing proprioceptive feedback, said tail means having a cross-sectional area at least about 30% of the maximum cross-sectional area portion of said body.

2. A device as recited in claim 1 further comprising a gliding sleeve remote from said body having interior cross sectional dimensions larger than the cross sectional dimensions of at least a portion of said tail means, and surrounding said portion of said tail means to allow sliding movement of said tail means with respect thereto.

3. A device as recited in claim 2 wherein said sleeve has means defining a longitudinal slit therein to allow said sleeve to be fit over a continuous loop of material.

4. A device as recited in claim 2 wherein said gliding sleeve comprises a tube of polyethylene.

5. A device as recited in claim 1 wherein said tail means comprise an integral loop of material continuously and uninterruptively extending from said first end of said body to said second end thereof.

6. A device as recited in claim 1 wherein said tail means comprise a first tail portion integral with said body first end and having a free end, and a second tail portion integral with said body second end and having a free end; and attachment means for attaching said free ends of said first and second tail portions together.

7. A device as recited in claim 1 wherein said tail means comprise a tail member integral with said body first end, and having a free end; and means for attaching said free end of said tail member to said second end of said body.

8. A device as recited in claim 5 wherein said tail means has a cross sectional area less than the cross sectional area of said body.

9. A device as recited in claim 1 wherein the cross sectional area of the radial exterior portion of said body is greater than the cross sectional area of the radial interior portion of said body.

10. A device as recited in claim 1 wherein said body is of a first material, and said tail means is of a second material, different than said first material.

11. A device as recited in claim 1 wherein said body has a shape, when implanted, of a naturally occurring meniscus.

12. A meniscus prosthetic device comprising an arcuate body of biocompatible, deformable, flexible and resilient material, said body having a radial interior portion and a radial exterior portion, each of said portions having a thickness, wherein said exterior portion has a thickness greater than the thickness of the radial interior portion of said body, the arcuate extent of said body being significantly less than 360°, but at least about 150°, and said body having first and second ends; and
a tail of biocompatible material, integral with said body at said first and second ends thereof, and extending so so that said body and tail together extend through a complete 360° arc.

13. A device as recited in claim 12 further comprising a tubular sleeve having an interim cross-sectional area greater than the exterior cross-sectional area of said tail, and disposed around at least a portion of said tail remote from said body.

14. A meniscus prosthetic device comprising an arcuate body of biocompatible, deformable, flexible and resilient material, said body having a radial interior portion and a radial exterior portion, each of said portions having a thickness, wherein said exterior portion has a thickness greater than the thickness of the radial interior portion of said body, said body having an arcuate extent of less than 360°, but at least about 150°, and said body having first and second ends, and said body having a maximum cross-sectional area portion; and tail means of biocompatible material integral with said body at at least one of said first and second ends thereof, said tail having a cross-sectional area between about 30-100% of the maximum cross-sectional area portion of said body.

15. A device as recited in claim 14 wherein said tail means comprises two tail portions one integral with each of said first and second ends of said body, and each having a free end; said free ends adapted to be knotted, or affixed together.

16. A device as recited in claim 14 wherein said tail means comprises a single tail portion integral with said first end of said body portion, and having a free end; said free end adapted to be connected to said second end of said body.

17. A meniscus prosthetic device to prevent and reverse degenerative changes in a human knee, for replacing natural components of a femoral condylar joint so that articular cartilage therein remains intact, said device comprising:

an arcuate body of biocompatible, deformable, flexible and resilient material for bearing compressive loads and for translating the loads to tensile stress, and for stabilizing the femoral condyle, and to lubricate and aid in metabolism of articular surfaces of a knee joint, said body having first and second ends, and a radial exterior portion and a radial interior portion; and tail means of biocompatible material extending as a continuation of said body from each of said first and second ends thereof, for providing a continuous loop circuit for propagation of tensile stresses from said body, for providing stabilization of the knee joint, and for providing proprioceptive feedback, said tail means comprising at least one integral element continuously and uninterruptively extending from at least one end of said body.

18. A device as recited in claim 17 wherein said body has a maximum cross-sectional area portion, and wherein said tail means has a cross-sectional area at least about 30% of the maximum cross-sectional area portion of said body.

19. A device as recited in claim 17 wherein said tail means comprises an integral element continuously and uninterruptively extending from at least said first end of said body.

20. A device as recited in claim 17 further comprising a gliding sleeve remote from said body having interior cross-sectional dimensions larger than a cross-sectional dimension of said tail means and surrounding a portion of said tail means to allow sliding movement of said tail means with respect thereto.

* * * * *